United States Patent [19]

Joyce, III et al.

[11] 4,133,823

[45] Jan. 9, 1979

[54] REACTION PRODUCTS OF METAL OXIDES AND SALTS WITH PHOSPHORUS COMPOUNDS

[75] Inventors: Samuel F. Joyce, III, Baldwin, Mo.; Albert W. Morgan, Collinsville, Ill.; Norman W. Touchette; William Vanderlinde, both of St. Louis, Mo.

[73] Assignee: Monsanto Company, St. Louis, Mo.

[21] Appl. No.: 724,192

[22] Filed: Sep. 17, 1976

Related U.S. Application Data

[63] Continuation-in-part of Ser. No. 553,947, Feb. 28, 1975, abandoned, which is a continuation of Ser. No. 223,275, Feb. 3, 1972, abandoned.

[51] Int. Cl.$^2$ .............................................. C07F 15/06
[52] U.S. Cl. ................................... 260/439 R; 106/16; 106/177; 260/45.7 P; 260/429 R; 260/429.3; 260/429.5; 260/429.9; 260/430; 260/431; 260/435 R; 260/438.1; 260/438.5 R; 260/446; 260/448 R; 260/448 B; 260/448.2 N; 260/931; 521/108; 521/85

[58] Field of Search ............ 260/439 R, 429 R, 429.3, 260/429.5, 438.5 R, 438.1, 429.9, 431, 435, 446, 448 R, 448.2 N, 430, 931, 439 R

[56] References Cited

U.S. PATENT DOCUMENTS

| | | | |
|---|---|---|---|
| 3,014,945 | 12/1961 | Birum | 44/69 X |
| 3,014,946 | 12/1961 | Birum | 260/931 |
| 3,014,951 | 12/1961 | Birum | 260/931 |
| 3,102,899 | 9/1963 | Cannell | 260/439 R |
| 3,290,348 | 12/1966 | Mullineaux | 260/439 |
| 3,463,835 | 8/1969 | Budnick | 260/439 R X |
| 3,534,125 | 10/1970 | Knollmueller | 260/932 |
| 3,678,086 | 7/1972 | Lynch et al. | 260/439 R |
| 3,705,191 | 12/1972 | Kerst | 260/502.4 |

*Primary Examiner*—Helen M. S. Sneed
*Attorney, Agent, or Firm*—George R. Beck; Robert E. Wexler; Edward P. Grattan

[57] ABSTRACT

Reaction products are prepared from metal oxides and salts and phosphorus compounds containing trivalent phosphorus. The reaction products are useful as flame retardants and smoke suppressants.

13 Claims, 2 Drawing Figures

(1) Tris (β-chloroethyl) phosphate
(2) Tris(2,3-dichloropropyl) phosphate
(3) 2,2-Bis-(chloromethyl) trimethylene bis[di(2-chloroethyl) phosphate]
(4) Tris (2,3-dibromopropyl) phosphate
(5) Reaction product of $CdCl_2$/phosphonate of Example 6 (1:20 molar)

4,133,823

REACTION PRODUCTS OF METAL OXIDES AND SALTS WITH PHOSPHORUS COMPOUNDS

CROSS REFERENCES TO RELATED APPLICATIONS

This application is a continuation-in-part of copending application, Ser. No. 553,947, filed Feb. 28, 1975, now abandoned which is a continuation of Ser. No. 223,295, filed Feb. 3, 1972, now abandoned.

BACKGROUND OF THE INVENTION

This invention relates to complex reaction products of metal oxides and metal salts with phosphorus compounds or mixture of same containing at least some trivalent phosphorus, their method of preparation and their use as flame retardants and smoke suppressants in synthetic and natural materials.

Heretofore, organometallic phosphorus compounds have been prepared by reacting various metal derivatives with phosphorus compounds. Thus, U.S. Pat. No. 2,228,653 discloses the preparation of organometal salts such as calcium cetyl phosphate by the reaction of a metal carbide, i.e., calcium carbide, and an organic phosphorus-containing acid. The organic acids disclosed as useful in the reaction include organic acids containing phosphorus in either the trivalent or pentavalent state. No utility is disclosed for the compounds.

U.S. Pat. No. 2,329,707 discloses the preparation of aluminum, chromium and tin salts of phosphorus acids containing pentavalent phosphorus by reacting the acid with an alkali metal hydroxide and then precipitating the desired metal salt from the solution of the alkaline salt by addition of aluminum, chromium or tin ion. The compounds are disclosed as useful as antioxidants, lubricating and drying oils and varnishes.

U.S. Pat. No. 2,411,671 discloses foam inhibiting compounds which are Group I metal salts of alkyl alkylene diphosphates containing pentavalent phosphorus.

U.S. Pat. No. 2,416,985 discloses Groups II, III, IV and VI metal salts of oxyacids of phosphorus-containing pentavalent phosphorus as stabilizing agents for lubricating oils.

U.S. Pat. No. 2,784,206 discloses metallo-vinyl phosphonates as stabilizers for polymeric materials.

U.S. Pat. No. 3,397,216 discloses coordination complexes of the halides of antimony, tin and titanium with pentavalent phosphorus compounds. The coordination complexes are disclosed as useful flame retardants for polymeric systems.

SUMMARY OF THE INVENTION

In accordance with the present invention, certain metal oxides and salts or salts of ammonia and silicon are reacted with one or more phosphorus compounds characterized by the presence of at least some trivalent phosphorus and by the absence of active protons or ionic halogens. The reaction products are extremely complex and are apparently composed of a partial metallic oxide or salt or ammonium or silicon salt of the phosphorus compound, a coordinate complex of the oxide or salt with the phosphorus compound and a partial solution of the oxide or salt in the phosphorus compound, such components being in dynamic equilibrium. The reaction products are extremely stable and heat resistant.

The reaction products of the invention are prepared by the reaction of metal oxides or salts or ammonium or silicon salts with mixtures of phosphorus compounds, at least one of which is characterized by the presence of trivalent phosphorus, or by the reaction of such oxides or salts with a phosphorus-containing compound characterized by the presence of both trivalent and pentavalent phosphorus. It is to be understood, however, that the reaction products are so complex that a simple definitive statement as to their physical and chemical structure, as set forth above, is theoretical only. It is entirely possible that specific oxides or salts may form reaction products with trivalent phosphorus compounds which may exist predominantly in one or more of the above-described phases.

Since the reaction products of this invention are extremely stable and highly heat resistant, their primary utility is as flame retardants and smoke suppressants. The reaction products of the invention do, in fact, impart outstanding flame retardant and smoke suppressant characteristics to a wide variety of materials. Additionally, however, amazingly varied applications have been found for the reaction products of the present invention. Thus, the reaction products may be used as reactive modifiers for epoxy resins, unsaturated polyesters and other polymeric materials, as adhesion promotors for asphalt-based rubber adhesives, as reactive modifiers and tackifiers for elastomeric materials, as antioxidants and sequestrating agents, as reactive additives for phenolics, as pigments and coloring agents, as agents for the electroless deposition of metals on metals and non-metals, as the basic component of printed circuits and metallic decorations, as an aluminum soldering flux, as corrosion inhibitors and rust removers, as stabilizers for vinyl resins, as tackifiers in resin formulations, as blowing agent aides, as ignition retarders, as adhesive agents for fusing plastisols to metal, as fungicides and insecticides and as heat absorbent coatings.

Accordingly, the objective of this invention is to provide novel, complex reaction products of metal oxides and salts or ammonium or silicon salts and trivalent phosphorus-containing compounds, their method of preparation and their use as flame retardants and smoke suppressants for natural and synthetic resins and resin plasticizers and materials prepared therefrom.

DESCRIPTION OF THE PREFERRED EMBODIMENT

Figure 1:
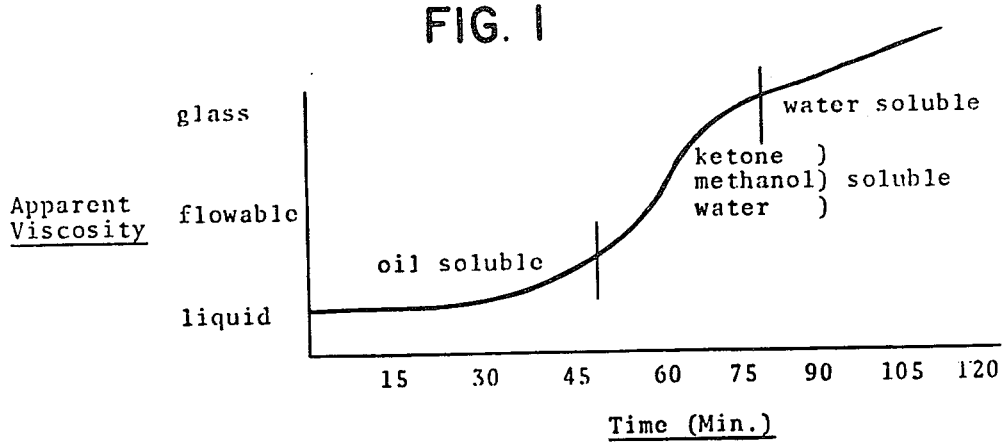

The objective of this invention is accomplished by reacting a metal oxide or salt or mixture thereof or ammonium or silicon salt with phosphorus compounds which contain reactant trivalent phosphorus but which, in order to avoid the formation of simple salts, do not contain active protons or ionically bound halogens.

The metal oxides and salts which are used to prepare the complex reaction products of this invention are the various salts of the Group IA metals, i.e., lithium, sodium, potassium, rubidium, cesium and francium; the Group IB metals, i.e., copper, silver and gold; Group IIA metals, i.e., magnesium, calcium, strontium and barium; the Group IIB metals, i.e., zinc, cadmium and mercury; the Group IIIB metals, i.e., aluminum, gallium and indium; the Group IVA metals, i.e., titanium, zirconium and hafnium; the Group IVB metals, i.e., germanium, tin and lead; the Group VA metals, i.e., vanadium, niobium and tantalum; the Group VB metals, i.e., arsenic, antimony and bismuth; the Group VIA metals, i.e., chromium, molybdenum and tungsten; the Group VIB metals, i.e., selenium, tellurium and polonium; the Group VIIA metals, i.e., manganese, technetium and rhenium; and the Group VIII metals, i.e., iron, cobalt, nickel, ruthenium, rhodium, palladium, osmium, iridium and platinum.

The preferred metal oxides and salts are those of the Group I metals, i.e., lithium, sodium, potassium and rubidium and copper, silver and gold; the Group II metals, i.e., strontium, calcium, barium, magnesium and zinc, cadmium and mercury; the Group III metals, i.e., aluminum; the Group IV metals, i.e., tin and lead and titanium and zirconium; the Group V metals, i.e., vanadium and antimony, the Group VI metals, i.e., chromium, molybdenium and tungsten; and the Group VIII metals, i.e., iron and ruthenium, cobalt and nickel, platinum and palladium. The metal groups referred to above correspond to the grouping of elements as set forth in the Revised Edition (1953) of the Periodic Chart of the Atoms (National Bureau of Standards), published by W. M. Welch Publishing Company.

The preferred oxides and salts of ammonia, silicon and of the above-described metals which are used to prepare the reaction products of the present invention include the halides, i.e., the chlorides, bromides and fluorides and mixtures thereof, including halide hydrates, the acetate salts, the oxides and oxyhalides, nitrates and cyanates, the phosphates and sulfates, the carbonates, bromates, bromometalates, e.g., bromoselenate, chromates, cyanides, ferrocyanides, fluoborates, iodates, nitrites and sulfites. Especially preferred anion moieties are halides, phosphates, carbonates, oxyhalides, halide hydrates, acetate, oxides, nitrates, cyanates, sulfates, chromates and bromates.

Specific ammonium and silicon salts and metal oxides and salts utilized in accordance with this invention include ammonium acetate, ammonium aluminum chloride, ammonium aluminum sulfate, ammonium bromate, ammonium bromide, ammonium bromoplatinate, ammonium bromoselenate, ammonium bromostannate, ammonium cadmium chloride, ammonium calcium arsenate, ammonium calcium phosphate, ammonium carbonate, ammonium chloride, ammonium chlorostannate, ammonium chromate, ammonium dichromate, ammonium cobalt sulfate, ammonium copper chloride, ammonium cyanate, ammonium cyanide, ammonium ferrocyanide, ammonium fluoborate, ammonium iodate, ammonium triodide, ammonium magnesium chloride, ammonium molybdate, ammonium nickel chloride, ammonium metavanadate, ammonium vanadium sulfate, ammonium zinc sulfate, actinium chloride, antimony tribromide, antimony trichloride, antimony pentachloride, antimony pentafluoride, antimony triiodide, antimony trioxide, antimonous oxychloride, antimonous dioxysulfate, antimony triselenide, antimonous sulfate, arsenic oxychloride, barium bromide, barium fluoride, barium bromoplatinate, barium carbonate, barium chloride, barium fluoride, barium hypochloride, barium chromate, barium fluoride, barium iodate, barium iodide, barium nitrate, barium nitrite, barium oxide, barium hypophosphate, barium tungstate, bismuth carbonate, cadmium acetate, cadmium bromide, cadmium carbonate, cadmium chloride, cadmium chloroacetate, cadmium ferrocyanide, cadmium fluoride, cadmium iodide, cadmium nitrate, cadmium oxide, cadmium phosphate, calcium acetate, calcium aluminate, calcium bromide, calcium carbonate, calcium chloride, and the calcium chloride mono-, di- and tri-hydrates, calcium chromate, calcium fluoride, calcium iodide, calcium magnesium carbonate, calcium nitrate, calcium oxide, calcium sulfate, calcium sulfite, cesium bromate, chromium acetate, chromous bromide, chromic bromide, chromous chloride, chromic chloride, chromous fluoride, chromic fluoride, chromous iodide, chromic nitrate, chromous oxide chromic sesquioxide, chromous sulfate, chromic sulfate, cobaltous acetate, cobaltous bromide, cobaltous chlorate, cobaltous chloride, cobaltic chloride, cobaltous chromate, cobaltous fluoride, cobaltic fluoride, cobaltous iodide, cobaltous nitrate, cobaltous oxide, cobaltic oxide, cobaltous sulfate, cuprice acetate, cupric bromide, cuprous bromide, cuprous carbonate, cuprous chloride, cupric chloride, cupric chromate, cuprous fluoride, cupric fluoride, cupric iodate, cuprous iodide, cupric nitrate, cuprous oxide, cupric oxide, cupric oxychloride, cuprous sulfate, cupric sulfate, cupric tungstate, aurous bromide, auric bromide, aurous chloride, auric chloride, aurous iodide, auric iodide, auric hydrogen nitrate, ferrous acetate, ferric acetate, ferrous bromide, ferric bromide, ferrous carbonate, ferrous chloride, ferric chloride, ferrous chlorplatinate, ferrous fluoride, ferric fluoride, ferrous iodide, ferrous nitrate, ferric nitrate, ferrous oxide, ferric oxide, ferrous sulfate, francium chloride, gallium ferrocyanide, germanium oxide, hafnium oxide, indium iodate, rirdium sulfate, lanthanum carbonate, lead acetate, lead bromide, lad chloride, lead iodide, lead oxychloride, lead sulfate, lead sulfite, lithium acetate, lithium bromide, lithium chloride, lithium fluoride, lithium iodide, lithium nitrate, magnesium acetate, magnesium bromide, magnesium chloride, magnesium iodide, mangesium carbonate, magnesium nitrate, magnesium sulfate, manganese acetate, manganese bromide, mercuric chloride, molybdenum dibromide, molybdenum tribromide, molybdenum tetrachloride, molybdenum pentachloride, molybdenum hexafluoride, molybdenum oxytrichloride, molybdenum metaphosphate, nickel acetate, nickel bromide, nickel chloride, nickel iodide, nickel carbonate, nickel nitrate, nickel sulfate, niobium pentafluoride, osmium sulfate, palladium bromide, palladium fluoride, palladium chloride, palladium iodide, palladium nitrate, palladium sulfate dihydrate, platinum diiodide, platinum sulfate, polonium chloride, potassium acetate, potassium bromide, potassium chloride, potassium iodide, potassium cadmium iodide, potassium calcium fluoride, potassium carbonate, potassium molybdate, potassium nitrate, potassium nitrite, potassium rhodium sulfate, potassium sulfate, potassium tungstate, radium sulfate, rhenium oxytetrachloride, rhodium oxide, ruthenium sulfate, rubidium acetate, rubidium aluminum sulfate, rubidium bromide, rubidium tribromide, rubidium chloride, rubidium dichlorobromide, rubidium fluorodibromide, rubidium carbonate, rubidium copper sulfate, rubidium fluoride, rubidium nitrate, rubidium sulfate, scandium sulfate, selenium oxide, disilicon hexachloride, silicon tetrafluoride, silicon tetraiodide, silicon tetrachloride, silver bromide, silver carbonate, silver iodide, silver nitrate, silver phosphate, silver sulfate, sodium acetate, sodium bromide, sodium chloride, sodium iodide, sodium carbonate, sodium chloroiodide, sodium nitrite, sodium phosphate, sodium sulfate, stannous bromide, stannic bromide, stannous chloride, stannic chloride stannous iodide, stannic iodide, stannous nitrate, stannic nitrate, stannous sulfate, strontium acetate, tantalum bromide, technetium chloride, tellurium iodide, titanium tetrachloride, titanium sulfate, tungsten hexafluoride, vanadium chloride, yttrium bromide, zinc acetate, zinc dibromide, zinc dichloride, zinc diiodide, zinc nitrate, zinc phosphate and zirconium sulfate.

It is to be understood that mixtures of salts or mixtures or oxides and salts may be used to prepare the reaction products of this invention.

Preferred salts include cobalt chloride tetrahydrate, cobalt chloride hexahydrate, cobalt acetate, cobalt chloride, cobalt sulfate, cadmium acetate, cadmium ferrocyanide, cadmium chromate, cadmium phosphate, cadmium chloride, copper chloride, copper acetate, copper nitrite, calcium chloride, calcium oxide, clacium permanganate, nickel chloride, nickel acetate, nickel sulfide, iron oxide, iron chloride, silver chloride, silver acetate, silver nitrate, manganese chloride, tin chloride, lead chloride, lead iodide, sodium sulfate, barium chloride, barium bromide, aluminum chloride, aluminum acetate, ammonium chloride, antimony chloride, antimony oxychloride, antimony oxide, chromium bromide, chromium sulfate, magnesium carbonate, magnesium bicarbonate, strontium chloride, molydenum tetrachloride, lithium chloride, palladium dichloride, platinum tetrachloride, potassium bromide, rubidium monochloride, ruthenium dichloride, zinc oxide, silicon tetrachloride and vanadium trichloride.

Phosphouus compounds containing trivalent phosphorus and characterized by the absence of active protons and ionic halogens are essential materials in the preparation of the reaction products of this invention. The phosphorus compounds containing trivalent phosphorus which are useful in accordance with this invention are set forth in the following, commonly-assigned, U.S. Pat. Nos. 3,014,910; 3,014,944; 3,014,945; 3,014,946; 3,014,947; 3,014,948; 3,014,950; 3,014,951; 3,014,954; 3,014,956; 3,029,271; 2,058,941 and 3,160,650, such patents being herein incorporated by reference in order to fully set forth and disclose the trivalent phosphorus-containing compounds which are utilized in accordance with this invention. Thus, U.S. Pat. No. 3,014,910, entitled "Nitrogenous Organic Compounds of Phosphorus" and patented Dec. 26, 1961, discloses phosphinyl phosphoramidites at column 1, lines 14 through 39, column 2, lines 20 through 72, column 3, and column 4, lines 1 through 70.

U.S. Pat. No. 3,014,944, entitled "Process of Preparing Organic Phosphorus Compounds" and patented Dec. 26, 1961, discloses compounds having both trivalent phosphorus and pentavalent phosphorus ester roups. Such compounds are disclosed at column 1, lines 23 through 35, column 2, lines 9 through 65, column 12, lines 23 through 38, column 13, lines 5 through 30, column 13, lines 65 through 75, columns 14 through 43 and Examples 1 through 104.

U.S. Pat. No. 3,014,945 is entitled "Triphosphinyl Phosphites" and was patented on Dec. 26, 1961. It provides novel triphosphinyl phosphites which are disclosed at column 1, lines 13 through 32, column 2, lines 10 through 72, columns 3 and 4, column 5, lines 1 through 37 and Examples 1 through 6.

U.S. Pat. No. 3,014,946 is entitled "Phosphinyl Diesters of Aromatic Phosphates" and was patented Dec. 26, 1961. It discloses such aromatic phosphites at column 1, lines 15 through 44, column 2, lines 59 through 71, columns 3 through 5, column 6, lines 1 through 18 and Examples 1 through 3.

U.S. Pat. No. 3,014,947 is entitled "Phosphinyl Diesters of Phosphonites" and was patented on Dec. 26, 1961. It discloses such phosphonites at column 1, lines 13 through 32, column 2, lines 23 through 72, column 3, column 4, lines 1 through 65 and Examples 1 through 4.

U.S. Pat. No. 3,014,948 is entitled "Cyclic Esters of Phosphorus Compounds" and was patented on Dec. 26, 1961. It discloses cyclic phosphorus esters containing trivalent phosphorus at column 1, lines 14 through 52, column 3, lines 61 through 75, columns 4 and 5, column 6, lines 1 through 34 and Examples 1 through 41.

U.S. Pat. No. 3,014,950 is entitled "aromatic Di-Functional Phosphorus Esters" and was patented Dec. 26, 1961. It discloses di-functional phosphorus esters containing trivalent phosphorus at column 1, lines 14 through 40, column 3, lines 25 through 75, columns 4 and 5, column 6, lines 1 through 46 and Examples 1 through 5.

U.S. Pat. No. 3,014,951 is entitled "Phosphite-Phosphonates" and was patented Dec. 26, 1961. It discloses phosphite-phosphonates having trivalent phosphorus at column 1, lines 15 through 60, column 6, lines 39 through 75, columns 7 through 10, column 11, lines 1 through 34 and Examples 1 through 43.

U.S. Pat. No. 3,014,954 is entitled "Polyphosphorus Esters and Method of Preparing Same" and was patented Dec. 26, 1961. It discloses polyphosphorus esters containing trivalent phosphorus at column 1, lines 17 through 72, columns 2 through 5, column 6, lines 1 through 50, column 8, lines 58 through 75, column 9, lines 1 through 53, column 10, lines 17 through 65, column 11, lines 65 through 75, column 12, lines 1 through 23, column 13, lines 6 through 29 and Examples 1 through 25.

U.S. Pat. No. 3,014,956 is entitled "Pentavalent Phosphorus Esters" and was patented Dec. 26, 1961. The pentavalent phosphorus esters of this patent are prepared by isomerization of trivalent phosphorus compounds disclosed at column 1, lines 53 through 72, column 2, lines 1 through 6, 19, 26 through 35, 53, 60 through 63, column 5, lines 5 through 11, 23 through 25, 31 through 36, 43 through 48, 56 through 60 and 69 through 75, column 4, lines 8 through 17, lines 23 through 31 and 53 through 75, column 5, lines 1 through 23, 35 through 75, column 6, column 7, lines 1 and 1, 13 through 23, lines 28 through 67, column 8, lines 1 through 5, lines 9 through 15, lines 21 through 28, lines 43 through 65, and lines 69 and 70, column 13, lines 65 through 73, column 15, lines 33 through 75, column 16, column 17, lines 1 through 67, column 18, lines 22 through 75, column 19, lines 70 through 75, column 20, lines 1 through 31, column 21, lines 13 through 22, lines 54 through 61, lines 66 through 72, column 22, lines 6 through 17 and Examples 1 through 25.

U.S. Pat. No. 3,029,271 is entitled "Organic Phosphorus Compounds" and was patented Apr. 10, 1962. It discloses phosphorus compounds containing trivalent phosphorus at column 1, lines 13 through 72, column 2, lines 3 through 27, column 3, lines 15 through 40 and lines 64 through 75, column 4, lines 1 through 69 and Examples 1 through 12.

U.S. Pat. No. 3,160,650 is entitled "Process for Making 1-Cyclohexenyl Phosphonic Acid Diesters and an Intermediate Compound for Use Therein" and was patented Dec. 8, 1964. It discloses trivalent phosphorus compounds at column 1, lines 40 through 67, column 2, lines 23 through 72, column 3, lines 1 and 2, column 6, lines 20 through 75, column 7, lines 1 through 42 and Examples 1 through 10.

The preferred trivalent phosphorus-containing compound which is utilized as a reactant in the process of the present invention is disclosed in U.S. Pat. No. 3,014,956, described above. In that patent, pentavalent phosphorus esters, i.e., phosphonates, are prepared by the isomerization of phosphite-phosphonates. Although, as described in that patent, isomerization yields phosphonate esters in which no trivalent phosphorus is present, it has been found that if the isomerization or conversion is not carried to completion, the final product is a mixture of nonisomerized phosphite-phosphonates and isomerized phosphonates. The specific portions of U.S. Pat. No. 3,014,956 which disclose the phosphite-phosphonates containing trivalent phosphorus have been identified above. Specific compounds which are preferred reactants in the present invention, however, include:

bis(2-chloroethyl) phosphite of bis(2-chloroethyl)1-hydroxyethylphosphonate
tris(2-chloropropyl) phosphite
triethylphosphite
alkyl diphenyl phosphite
bis(2-chloro-4-phenoxybutyl) methyl phosphite
trimethyl phosphite
triethyl phosphite
triallyl phosphite
triisopropyl phosphite
tri-n-propyl phosphite
tri-2-butenyl phosphite
tri-n-butyl phosphite
tri-tert-amyl phosphite
tri-n-hexyl phosphite
tri-n-heptyl phosphite
tris(2-ethylhexyl) phosphite
trioctenyl phosphite
tri-n-octyl phosphite
trinonyl phosphite
tridecyl phosphite
triundecyl phosphite
tri-tert-dodecyl phosphite
tridodecenyl phosphite
amyldiethyl phosphite
butyl di-n-propyl phosphite
n-dodecyl dimethyl phosphite
ethyl octyl propyl phosphite
tris(2-chloroethyl) phosphite
tris(3-chloropropyl) phosphite
tris(2-chloropropyl) phosphite
tris(3,4-dichlorobutyl) phosphite
tris(2-chloro-4-pentenyl) phosphite
tris(2-bromoethyl) phosphite
tris(3-chloro-2-propenyl) phosphite
tris(3-iodylpropyl) phosphite
tris(2-chloroethyl) phosphite
tris(dichlorododecyl) phosphite
tris(2-ethoxyethyl) phosphite
2-chloroethyl diethyl phosphite
tris(2-phenoxypropyl) phosphite
3-bromopropyl bis(2-chloroethyl) phosphite
diamyl trichlorooctyl phosphite
2-chloroethyl phosphite
3-chloropropyl phosphite
4-chlorobutyl phosphite
2-chloroethyl methyl propyl phosphite
tris(2,3-dichloropropyl) phosphite
tris(2-bromo-3-chloropropyl) phosphite
tris(2-chloro-3-methoxypropyl) phosphite
tris(2-bromo-4-phenoxybutyl) phosphite Instead of the above-described tribasic phosphites, there may be employed certain phosphonites, i.e., diesters of hydrocarbyl or halohydrocarbyl phosphonites, such as dimethyl phenyl phosphonite
diethyl phenyl phosphonite
diethyl 2-propinyl phosphonite
ethylmethyl phenyl phosphonite
di-n-propyl methyl phosphonite
di-n-butyl benzyl phosphonite
bis(2-chloroethyl) p-tolyl phosphonite
bis(2-methoxyethyl) cyclohexyl phosphonite
diethyl n-propyl phosphonite
bis(2-bromo-3-ethoxypropyl) 2-bromo-ethyl phosphonite
diethyl 2-propinyl phosphonite
bis(2-butyloctyl) 2-butenyl phosphonite
di-n-hexyl p-biphenyl phosphonite
diundecyl n-hexyl phosphonite
bis(trichloropropyl) 2-methyl cyclopentyl phosphonite
diethyl 4-n-hexylamyl phosphonite
diallyl 2-phenylethyl phosphonite
dipentenyl 2-ethylhexyl phosphonite
bis(2-chloroethyl) phenyl phosphonite
bis(tetrachloropentyl) ethyl phosphonite
bis(3-bromopropyl) biphenylyl phosphonite
bis(2-chloroethyl) benzyl phosphonite
bis(2-bromo-3-chloropropyl) phenyl phosphonite
allyl propyl 2,4-dichlorophenyl phosphonite
bis(trichlorooctyl) cyclohexyl phosphonite
bis(4-fluorobutyl) 2-cyclohexenyl phosphonite
bis(4-chlorobutyl) ethyl phosphonite
bis(dichlorohexyl) phenyl phosphonite
bis(2-chloropropyl) n-butyl phosphonite
di-n-butyl pentachlorophenyl phosphonite Alkyl and alkenyl dihydrocarbyl phosphinites are also useful in preparing the reaction products of the present invention. Typical phosphinites which may be used include the alkyl or alkenyl dihydrocarbyl phosphinites such as ethyl, allyl, butyl, n-octyl, and diethyl phenyl phosphinites or diphenyl or ditolyl phosphinite, benzyl cyclohexyl phosphinite or diallyl phosphinite; the corresponding haloalkyl esters such as 2-chloropropyl-di-p-tolyl phosphinite or 2-fluoroethyl ethylmethyl phosphinite; the ether-substituted esters such as 4-methoxybutyl or 3-phenoxy-2-chloropropyl di-n-butyl phosphinite or di-β-naphthyl phosphinite; and the corresponding esters of the halosubstituted phosphinic acids such as the methyl, pentyl, ethyl, 2-butenyl, 2-chloroethyl, 3-methoxypropyl or 4-butoxy-2-bromopentyl esters of bis(2-chloropropyl) phosphinite or of n-butyl (4-chlorophenyl) phosphinite.

A preferred phosphorus compound is a phosphonate/phosphite compound disclosed in U.S. Pat. No. 3,014,956, described above. It has the formula

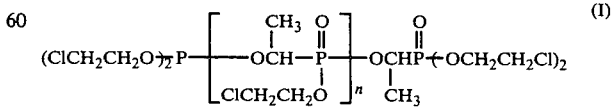 (I)

wherein n has a value from 0 to 4 and preferably has a value of 1 or an average value of 2.

Equally preferred is the mixture of phosphorus compounds resulting from the incomplete conversion of isomerization of the compound of formula (I) to the phosphonate. The compound of formula (I) is converted to the phosphonate by the application of heat at about 190–200° C. for a short time, i.e. ¼ to 2 hr. The phosphonate has the formula

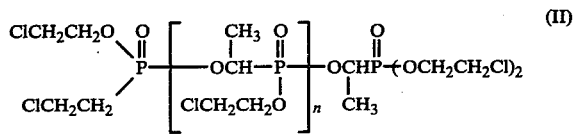

wherein n has a value from 0 to 4 but preferably has a value of 1 or an average value of 2.

By controlling the time and temperature at which compound (I) is heated, a mixture is obtained which may vary from 99 percent compound (I) and 1 percent compound (II) to 99 percent compound (II) and 1 percent compound (I). Best results are obtained by using compound (I) alone or by using a mixture of compounds (I) and (II) wherein the mixture contains at least 0.05 percent trivalent phosphorus and preferably from about 1 to about 10 percent trivalent phosphorus.

The conditions under which the reaction of the phosphorus-containing compound and the oxide or salt takes place are not critical. Thus, the phosphorus-containing compound and the oxide or salt are merely mixed together at ambient temperature and pressure. Under certain conditions, heating may be necessary to effect a more complete dissolution of the oxide or salt in the phosphorus-containing compound and thus insure a more complete and homogenous reaction.

The molar ratio of oxide or salt to total phosphorus compounds may be from 1:1 to 1:20 or greater. Preferably, the ratio is from about 1:4 to about 1:10.

The following, non-limiting examples will serve to illustrate the specific embodiments of the reaction products of the present invention and their preparation. In the examples, the percent of trivalent phosphorus present is determined by dividing the percent phosphite-phosphonate compound present by the number of phosphorus atoms in the phosphite-phosphonate compound. Thus, if there is 0.5 percent phosphite-phosphonate compound present, the number of phosphorus atoms in that compound would be 2 if n=0, 3 if n=1, 4 if n=2, 5 if n=3 and 6 if n=4. Accordingly, if n=1, one would divide 0.5 percent by 3 to determine the percent of trivalent phosphorus present.

EXAMPLE 1

A mixture of 63.8 g. of phosphonate (n=1) containing 0.5 percent of phosphite-phosphonate and 26.7 g. cobaltous chloride tetrahydrate is heated at 150° C., with stirring, for four hours. A creamy, dark blue layer separates and is recovered, washed with toluene and dried for one hour at 170° C. The material is water-soluble and tacky.

EXAMPLE 2

A mixture of 126 g. of phosphonate (n=1) containing 1.0 percent of phosphite-phosphonate and 28 g. of cadmium acetate is heated, with stirring, at 200° C. for two hours. Aliquots are taken at 15 minute intervals. The viscosity of the aliquots is plotted versus time in FIG. 1:

This example illustrates the great variety of products which are obtained in accordance with this invention. Complex reaction products are obtained which range from liquids to glasses and from oil soluble to water soluble. Using the same reactants, a variety of products are obtained as a result of variation in reaction time.

EXAMPLE 3

A variety of products are prepared by reacting a phosphonate (n=1), containing 0.5 percent of phosphite-phosphonate, and the salts listed below. Thus, a reaction mixture containing 10 moles phosphonate and 1 mole salt is heated at 150° C. for four hours to afford various colored reaction products:

| Salt | Color of Reaction Product |
|---|---|
| $CuCl_2$ | green/black |
| $CoCl_2$ | blue |
| $CdCl_2$ | water white |
| $CaCl_2$ | red |
| $NiCl_2$ | blue/green |
| $Cu(CO_2CH_3)_2$ | yellow |
| $Co(CO_2CH_3)_2$ | purple |
| $Ni(CO_2CH_3)_2$ | blue |
| $Cd(CO_2CH_3)_2$ | water white |

EXAMPLE 4

Example 3 is repeated at a reaction temperature of 70° C. Results are identical.

EXAMPLE 5

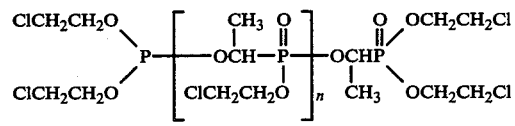

, where n may vary from 0 to 4, but is preferably 1, is mixed with various metal oxides and salts at a 10:1 molar ratio. The mixtures are heated at 180° C. until solution occurs or a change in viscosity is noted, with a five minute heating limit. Results are set forth below:

| Oxide or Salt | Color | Viscosity |
|---|---|---|
| CaO | opaque, white | solid |
| ZnO | clear | very viscous |
| $Cd(CO_2CH_3)_2$ | clear | high |
| $Co(CO_2CH_3)_2$ | purple | glassy |
| $Ni(CO_2CH_3)_2$ | clear, yellow-green | glassy |
| $CuCl_2$ | clear | glassy |
| $NiCl_2$ | yellow | glassy |
| AgCl | clear | medium increase |
| $SnCl_2$ | gray | glassy |
| $HgCl_2$ | gray, opaque | paste |
| $PbCl_2$ | clear | slight increase |
| $Ag(CO_2CH_3)_2$ | red | slight increase |
| $CoCl_2$ | blue | medium increase |
| $BaCl_2$ | clear | gel |

It is contemplated that similar reactions would occur using other oxides and salts such as LiCl, $Na_2SO_4$, KCl, $MgCO_3$, $TiCl_4$, $ZrCl_4$, $VBr_3$, CrBr, $MoO_2$, $WCl_2$, $MnO_2$, $FeCl_3$, $PdI_2$, $PtF_5$, $AlPO_4$, $AuCl_3$, $RuCl_2$, RbCl and $SrCl_2$.

EXAMPLE 6

Reaction products are prepared by heating the various inorganic salts listed below, for 60 minutes, with a phosphonate of the formula:

$$\begin{array}{c} ClCH_2CH_2O \\ \diagdown \\ \diagup \\ ClCH_2CH_2 \end{array} \!\! \overset{O}{\underset{\|}{P}} \!\!-\!\! OCH \!\!-\!\! \overset{O}{\underset{\|}{P}} \!\!-\!\! OCHP \!\! \begin{array}{c} \diagup OCH_2CH_2Cl \\ \diagdown OCH_2CH_2Cl \end{array}$$
$$\qquad\qquad ClCH_2CH_2O \quad CH_3$$

The phosphonate is prepared by incomplete isomerization of a phosphite-phosphonate of the formula:

$$\begin{array}{c} ClCH_2CH_2O \\ \diagdown \\ P \\ \diagup \\ ClCH_2CH_2O \end{array} \!\!-\!\! OCH \!\!-\!\! \overset{O}{\underset{\|}{P}} \!\!-\!\! OCHP \!\! \begin{array}{c} \diagup OCH_2CH_2Cl \\ \diagdown OCH_2CH_2Cl \end{array}$$
$$\qquad\qquad ClCH_2CH_2O \quad CH_3$$

The amount of trivalent phosphorus-containing phosphite-phosphonate in the phosphonate is a function of the degree of completeness of the isomerization procedure.

The oxides and salts utilized are:

| | | | |
|---|---|---|---|
| $BaCl_2$ | $AlCl_3$ | $MgCO_3$ | KBr |
| $Cu(NO_3)_2$ | $Al(OH)(CO_2CH_3)_2$ | $Mg(HCO_2)_2 \cdot H_2O$ | RbCl |
| $Cd_2Fe(CN)_6$ | $NH_4Cl$ | $MnCl_2$ | $RuCl_2$ |
| $CdCr_2O_4 \cdot 3H_2O$ | $SbCl_3$ | $MoCl_4$ | $SiCl_4$ |
| $Cd_3(PO_4)_2$ | SbOCl | $Ni_2S$ | $Ag_3(C_6H_5O_7)_2$ |
| $Ca(MnO_4)_2 \cdot 4H_2O$ | $Sb_2O_3$ | $PdCl_2$ | $Na_2SO_4$ |
| CrBr | $AuCl_3$ | $PtCl_4$ | $SrCl_4$ |
| $Cr_2(SO_4)_3$ | $BaBr_2$ | AgCl | $VCl_3$ |
| $Co_2(SO_4)_3$ | $Fe_2O_3$ | | |
| | $PbI_2$ | | |
| | LiCl | | |

Additional metal compounds which may be utilized are NaCl, $TiCl_4$, $ZrCl_4$, $WCl_2$, ZnO and $HgCl_2$.

The following, non-limiting examples illustrate embodiments of the flame retardant and smoke suppressant characteristics of the reaction products of the present invention. It should be noted that, insofar as the effect of fire on humans, flame is far less dangerous, comparatively, than smoke and noxious gases. By far the larger proportion of humans are killed by smoke and gases than by flame of fires; accordingly, the smoke suppressant characteristics of the present reaction products are considered equally important, if not more important, than their flame retardant characteristics.

Further, it should be noted that flame retardance and smoke suppression are antithetical characteristics. Due to the nature of flame and smoke propagation, increased flame indicates more complete combustion with a subsequent lowering of particulate matter and an increase in the ratio of the gas carbon dioxide to the significantly more lethal gas carbon monoxide. When flame is suppressed, oxidation is less complete, toxic concentrations of carbon monoxide quickly increase and visible smoke increases. Lowering smoke concentrations without greatly increasing flame, is consequently, an outstanding technical achievement.

EXAMPLE 7

The reaction product of Example 1 is incorporated into plastisols of the following formulations:

| Ingredients | 1 | 2 | 3 |
|---|---|---|---|
| Vinyl chloride/vinyl acetate (95:5) | 100 | 100 | 100 |
| Dioctyl phthalate (DOP) | 65 | 65 | 65 |
| Example 1 reaction product | 5 | 5 | — |
| Ba/Cd stabilizer | 1 | — | — |
| Epoxidized soya oil | 3 | — | — |

-continued

| Ingredients | 1 | 2 | 3 |
|---|---|---|---|
| Phosphonate[1] | — | — | 5 |

[1]Formula (II) where n=1.

The plastisols are fused on a metal hot plate. Formulations 1 and 2 are stable after one hour at 120° C. while formulation 3 discolors badly.

The reaction product of the invention imparts heat stability equivalent to a combination of standard heat stabilizers, i.e., Ba/Cd and expoxidized soya oil. Additionally, the reaction product apparently increases the heat stability of the phosphonate.

EXAMPLE 8

Samples of the reaction product of Example 2, taken at 30, 60 and 120 min., are incorporated, at 5 phr, in a 70 phr DOP/vinyl chloride-vinyl acetate plastisol. No heat stabilizer is used. All samples are fused at 185° C. for four minutes on a steel plate. None discolored and all are compatible with the plastisol. A control, containing only 70 phr DOP/Opalon 440, discolored badly.

A horizontal burn test is run (15 sec, gas burner ignition) on 4 × 6" samples of the plastisol. Results are shown below:

| Sample | Time to Self-Extinguishing (Seconds) |
|---|---|
| 30 min | 19 |
| 60 min | 15 |
| 120 min | 18 |
| Control | 75 |

The horizontal burn test is described in paragraph S5 of MVSS302 (Motor Vehicle Safety Standard No. 302).

In accordance with that test, a material which stops burning within 60 seconds of ignition meets governmental safety standards.

EXAMPLE 9

A mixture is prepared containing 22.8 g. $SbCl_3$ and 101.6 g. of a 60 percent solution of a phosphite-phosphonate of the formula $$\begin{array}{c} ClCH_2CH_2O \\ \diagdown \\ P \\ \diagup \\ ClCH_2CH_2O \end{array} \!\!-\!\! \overset{CH_3}{\underset{|}{OCH}} \!\!-\!\! \overset{O}{\underset{\|}{P}} \!\!-\!\! OCHP \!\! \begin{array}{c} \diagup OCH_2CH_2Cl \\ \diagdown OCH_2CH_2Cl \end{array}$$
$$\qquad\qquad ClCH_2CH_2O \quad CH_3$$

in ethyl chloride. The mixture is stirred for one hour at 70° C. A clear, very stable solution is formed.

The solution is mixed into a standard polyvinyl chloride plastisol screening formula containing 100 parts by weight PVC and 67 phr dioctyl phthalate. The solution is added to the plastisol at a concentration of one phr.

Film cast from the screening formula, containing 1 phr of the reaction product described above, is self-extinguishing within the test standard of the vertical burn test of Example 10.

EXAMPLE 10

A mixture of 92 g. antimony trichloride and 410 g. of the phosphite-phosphonate of Example 9 is stirred while heating at 100° C. for 1½ hours.

A standard screening formula of 100 parts by weight polyvinyl chloride and 67 phr dioctyl phthalate is prepared and to it is added one phr of the reaction product obtained above. A control sample is prepared containing only polyvinyl chloride and dioctyl phthalate.

During a 15 second ignition period, the control ignites and burns totally during a vertical burn test. The sample containing 1 phr of the above reaction product does not ignite.

Additionally, a cotton cloth is soaked with a 3 percent acetone solution of the reaction product and dried for 15 min. at 70° C. The cloth is not ignitable.

Vertical Burn Test Procedure

A specimen measuring one inch wide and 12 inches long is vertically mounted in a cabinet. The lower end of the specimen is exposed for 15 seconds to a 1½ inch flame from a ⅜ inch diameter barrel Bunsen burner supplied with natural gas. The specimen should not burn over a maximum of 90 seconds. Time of burning and inches burned are recorded.

EXAMPLE 11

The following flexible polyurethane foam formulations are prepared:

| Ingredients | Formulation Weight (grams) | |
|---|---|---|
| | 1 | 2 |
| Polyol | 100 | 100 |
| Water | 3.2 | 3.2 |
| Triethylenediamine | 0.45 | 0.45 |
| Polymethyl siloxane | 1 | 1 |
| Stannous octoate | 0.15 | 0.15 |
| Toluene diisocyanate | 48 | 48 |
| Reaction product[1] | 0 | 15 |

[1]Reaction product of 92 g. SbCl$_3$ and 410 g. of phosphite-phosphonate of Example 9.

A sample formulations 1 and 2 is subjected to ASTM 1692 which is the most widely used burning test for cellular plastics. In such test, a specimen (6 inches ×2 inches × ½inch) is supported on a horizontal hard-cloth support with the ½inch dimension vertical.

One end is contacted for 60 seconds with a 1½ inch high blue flame from a ⅜inch diameter barrel Bunsen burner fitted with a 1⅞ inch wide wingtop.

If the specimen instantly goes out, it is self-extinguishing. If the specimen burns and subsequently goes out, it is characterized as self-extinguishing/burn rate given as inches and seconds burned. If the specimen completely burns, its burn rate in inches/minute is given.

In the above test, Formulation 2 is self-extinguishing. Formulation 1, 6 inches/10 seconds.

Similar results are attained using the reaction product of the phosphite-phosphonate of Example 9 and SbCl$_3$ in molar ratios of 1:1, 2:1 and 4:1.

EXAMPLE 12

The following flexible polyurethane foam formulations are prepared:

| Ingredients | Formulation Weight (grams) | | |
|---|---|---|---|
| | 1 | 2 | 3 |
| Polyol | 100.00 | 100.00 | 100.00 |
| Triethylene diamine | 0.65 | 0.65 | 0.65 |
| Polymethyl siloxane | 1.00 | 1.00 | 1.00 |
| Water | 3.20 | 3.20 | 3.20 |
| Toluene diisocyanate | 54.00 | 54.00 | 54.00 |
| Stannous octoate | 0.25 | 0.25 | 0.25 |
| Reaction Product[1] | 0.15 | 0.15 | 0.15 |

[1]Reaction product of SnCl$_2$ and phosphite-phosphonate of Example 9 in 1:1 molar ratio (Formulation 1), 3:5 molar ratio (Formulation 2) and 1:4 molar ratio (Formulation 3).

All of the foams are self-extinguishing in accordance with the standards of ASTM 1692.

Similar results are attained with a reaction product of CdCl$_2$ and the phosphite-phosphonate of Example 9.

EXAMPLE 13

Polyurethane foams are prepared from the following formulations:

| Ingredients | Formulation Weight (grams) | | | | | | |
|---|---|---|---|---|---|---|---|
| | 1 | 2 | 3 | 4 | 5 | 6 | 7 |
| Polyol | 100.00 | 100.00 | 100.00 | 100.00 | 100.00 | 100.00 | 100.00 |
| Triethylene diamine | 0.65 | 0.65 | 0.65 | 0.65 | 0.65 | 0.65 | 0.65 |
| Water | 3.20 | 3.20 | 3.20 | 3.20 | 3.20 | 3.20 | 3.20 |
| Polymethyl siloxane | 1.00 | 1.00 | 1.00 | 1.00 | 1.00 | 1.00 | 1.00 |
| Toluene diisocyanate | 42.50 | 42.50 | 42.50 | 42.50 | 42.50 | 42.50 | 42.50 |
| Stannous octoate | 0.30 | 0.30 | 0.30 | 0.30 | 0.30 | 0.30 | 0.30 |
| Reaction Product[1] | 0.15 | 0.15 | 0.15 | 0.15 | 0.15 | 0.15 | 0.15 |

[1]Reaction Product 1 = CoCl$_2$ + Phosphite-phosphonate of Example 9 (1:2)
Reaction Product 2 = CoCl$_2$ 6H0 + Phosphate-phosphonate of Example 9 (1:2)
Reaction Product 3 = CdCl$_2$ + Phosphite-phosphonate of Example 9 (1:2)
Reaction Product 4 = NiCl$_2$ + Phosphite-phosphonate of Example 9 (1:4)
Reaction Product 5 = ZnCl$_2$ + Phosphite-phosphonate of Example 9 (1:2)
Reaction Product 6 = NiCl$_2$ + Phosphite-phosphonate of Example 9 (1:2)
Reaction Product 7 = SbCl$_3$ + Phosphite-phosphonate of Example 9 (1:2)
All foams are self-extinguishing according to ASTM 1692.

EXAMPLE 14

The foam formulation of Example 13 is repeated substituting 0.15 parts of the following reaction products:

1. SbCl$_3$ + Phosphonate of Example 6 (1:4)
2. SnCl$_2$ + Phosphonate of Example 6 (1:4)
3. SbCl$_3$ + Phosphonate of Example 6 (1:2)
4. CoCl$_2$ + Phosphite-phosphonate of Example 9 (1:2)
5. CdCl$_2$ + phosphite-phosphonate of Example 9 (1:2)

6. NiCl$_2$ + Phosphite-phosphonate of Example 9 (1:4)
7. SbCl$_3$ + Phosphite-phosphonate of Example 9 (1:2)

The seven formulations are subjected to ASTM 1692 with the following results:

| Formulation | Inches Burned | Flame Out (Seconds) |
|---|---|---|
| Control | Total | 300+ |
| 1 | 1.5 | 11 |
| 2 | 1.5 | 25 |
| 3 | 3.0 | 17 |
| 4 | 0.5 | 15 |
| 5 | 2.5 | 40 |
| 6 | 1.5 | 27 |
| 7 | 3.0 | 35 |

EXAMPLE 15

Vinyl foams are prepared from the following formulation:

| Ingredients | Weight (grams) |
|---|---|
| Vinyl chloride/vinyl acetate copolymer (95:5) | 60 |
| Blending resin | 40 |
| Phthalate blend plasticizer | 40 |
| Dibasic lead phosphate | 2 |
| Silicone prefoamer | 4 |
| Reaction prodcut[1] | 5 |

[1]
1. SbCl$_3$ + Phosphonate of Example 6
2. Cd(OAC)$_2$ + Phosphonate of Example 6
3. CdCl$_2$ + Phosphonate of Example 6
4. SnCl$_2$ + Phosphonate of Example 6
5. Ca(OAC)$_2$ + Phosphonate of Example 6
6. Control - no reaction product The formulations are subjected to flame spread and smoke generation tests.

The flame spread value is determined by observing the flame spread of an ignited test panel in a calibrated two-foot flame tunnel as compared with a standard which is determined by observing the maximum flame advance along the surface of preconditioned red oak and asbestos cement board prior to evaluation of the test samples. Construction and calibration of the flame tunnel and details concerning the flame spread test are given in the *Journal of Paint Technology*, Volume 39, No. 511, August, 1967. Red oak and asbestos have been assigned arbitrary flame ratings of 100 and zero, respectively.

The smoke rating procedure is described in ASTM/E-84 and involves the standardized burning of test samples using a photoelectric detector attached to a recorder to plot the smoke evolution of the sample. The data recorded from the burning sample are extrapolated via a linear relationship to stadarized smoke generation curves for asbestos cement board and preconditioned red oak. Asbestos board and red oak have been assigned arbitrary smoke ratings of zero and 100, respectively, or may also be described as the percent of light transmitted through the smoke.

The results are tabulated below, wherein the smoke rating is the percent of light transmitted through the smoke.

| Formulation Containing | Flame Rating | Smoke |
|---|---|---|
| Reaction Product 1 | 186 | 73 |
| Reaction Product 2 | 102 | 75 |
| Reaction Product 3 | 93 | 80 |
| Reaction Product 4 | 97 | 84 |
| Reaction Product 5 | 88 | 67 |
| Control | 104 | 64 |

The data show that the flame rating is equivalent to or better than the control in every case except Reaction Product 1.

More importantly, the smoke rating is superior to the control in every case. Reaction Products 3 and 4 are outstanding.

The efficacy of the reaction products of the invention as smoke suppressants withot attendant loss of flame retardancy (with the exception of Reaction Product 1) is clearly shown.

EXAMPLE 16

The following formulation is prepared:

| Ingredients | Parts (Weight) |
|---|---|
| Polyol | 100 |
| Toluene diisocyanate | 54 |
| Triethylene diamine | 0.65 |
| Water | 4 |
| Polymethyl siloxane | 1 |
| Stannous octoate | 0.25 |
| Reaction product[1] | 15 |

[1]Reaction product 1 = Phosphite-phosphonate of Example 9 + SbCl$_3$ (1:2 molar)
Reaction product 2 = Phosphite-phosphonate of Example 9 + NiCl$_2$ (1:2 molar)
Reaction product 3 = Phosphonate of Example 7 + SbCl$_3$ (1:2 molar)
Reaction product 4 = Phosphonate of Example 7 + SbCl$_3$ (1:10 molar)
Reaction product 5 = Phosphonate of Example 7 + CdCl$_2$ (1:20 molar)
Reaction product 6 = Phosphonate of Example 7 + SnCl$_2$ (1:20 molar)
Control = Phosphonate of Example 7

The six formulations are subjected to ASTM 1692 and MVSS 302. ASTM 1692 is a more stringent test since the wire mesh support used therein tends to hold molten material, thus supplying fuel. The horizontal burning of MVSS 302 allows burning material to fall away.

Heat stability at 140° C. is measured by:
(a) development of color and
(b) loss of physicals (i.e., crumbling of sample when compressed).

In the heat stability test, samples are placed in a circulating oven at a temperature of 140° C. Samples are tested at 30 minute intervals.

The results of ASTM 1692, MVSS 302 and heat stability tests are tabulated below:

| Sample Containing | Flame Retardancy | | Heat Stability (140° C.) |
| | Fresh | Aged 22 hrs at 140° C. | |
|---|---|---|---|
| Reaction Product 1 | 4–6"/min - ASTM 1692<br>S.E.[1] - MVSS 302 | S.E. - ASTM 1692<br>— | >30 hrs.<br><40 hrs. |
| Reaction Product 2 | 4"/min - ASTM 1692<br>S.E. - MVSS 302 | S.E. - ASTM 1692<br>— | >22 hrs.<br><30 hrs. |
| Reaction Product 3 | 4–6"/min - ASTM 1692<br>S.E. - MVSS 302 | S.E. - ASTM 1692<br>— | 28 hrs.<br>— |
| Reaction Product 4 | 4"/min - ASTM 1692<br>S.E. - MVSS 302 | S.E. - ASTM 1692<br>— | 35 hrs.<br>— |
| Reaction Product 5 | S.E. - ASTM 1692<br>— | S.E. - ASTM 1692<br>— | >64 hrs.<br>— |

-continued

| Sample Containing | Flame Retardancy | | Heat Stability (140° C.) |
| --- | --- | --- | --- |
| | Fresh | Aged 22 hrs at 140° C. | |
| Reaction Product 6 | S.E. - ASTM 1692 | S.E. - ASTM 1692 | 30 hrs. |
| Control | 10"/min - ASTM 1692 | — | 10 hrs. |

[1]S.E. = self-extinguishing

EXAMPLE 17

Using the formulation of Example 16, comparative heat stability and flame retardance (ASTM 1692) of samples is determined, using the reaction product of $CdCl_2$ and the phosphonate of Example 6 and conventional flame retardant materials.

Figure 2:
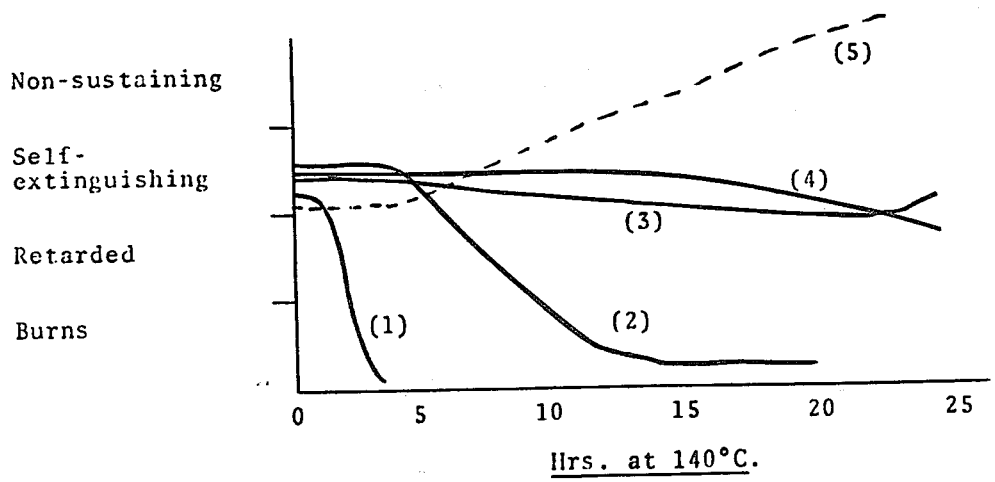

Results are shown in FIG. 2:

The preferred polymers utilized herein are plastisol and organosol formulations prepared from vinyl polymers. As is well known, plastisols are fluent mixtures of particulate vinyl resins and high boiling organic plasticizers therefor which are substantially non-solvents for the vinyl resin at ordinary temperatures, i.e., not over 35° C., but which are capable of dissolving the resin at high temperatures, i.e., above 35° C. and, more commonly, from 120–205° C. to form a fused thermoplastic film, sheet, layer or coating. Additionally, the vinyl plastisol may be foamed to provide an open or closed cell structure by expanding the plastisol and then heating to gel and fuse the expanded cellular structure. Such foam is generally produced by one of three methods. In the compressed gas method, a gas, such as carbon dioxide or nitrogen, is dissolved in the plastisol under pressure. Upon release of the pressure, the dissolved gas expands in the plastisol to form the plastisol into a closed cell vinyl sponge. A further process involves the use of chemical blowing agents which decompose in the plastisol to release a gas, such as nitrogen within the plastisol to form a foam or sponge structure. A further method for forming vinyl foam involves mechanical beating or frothing of a plastisol to incorporate air therein. These methods can also be used to prepare foams from other polymeric materials, such as polyurethanes.

The materials which are flame retarded and smoke suppressed in accordance with this invention include any of the conventional natural or synthetic thermoplastic or thermosetting normally solid polymers used for industrial purposes. Preferably, the thermoplastic resin is a polymer of vinyl chloride or a self-blowing polymer such as polyurethane. The vinyl chloride polymers can either be simple, unmixed homopolymers of vinyl chloride or copolymers or terpolymers in which the simple polymeric structure of polyvinyl chloride is interspersed at intervals with the residues of other ethylenically unsaturated compounds copolymerizable therewith. The essential properties of the polymeric structure of polyvinyl chloride are retained if not more than about 40 percent of a comonomer is copolymerized therewith. Suitable comonomers include vinyl halides such as vinyl bromide or vinyl fluorides; vinyl esters such as vinyl acetate, vinyl chloroacetate, vinyl butyrate and fatty acid vinyl esters; vinyl alkyl sulfonates; trichloroethylene; vinyl ethers such as vinyl ethyl ether, vinyl isopropyl ether and vinyl chloroethyl ether; aromatic and cyclic unsaturated compounds such as styrene, the mono- and polychlorostyrenes, coumarone, indene, vinyl naphthalene, vinyl pyridine, vinyl pyrrole; acrylic acid and its derivatives such as ethyl acrylate, methyl methacrylate, ethyl methacrylate, ethyl chloroacrylate, acrylonitrile and methacrylonitrile; vinylidene compounds such as vinylidene chloride, vinylidene bromide, vinylidene fluorochloride; unsaturated hydrocarbons such as ethylene, propylene and isobutenes; allyl compounds such as allyl acetate, allyl chloride and allyl ethyl ether; conjugated and cross-conjugated ethylenically unsaturated compounds such as butadiene, isoprene, chloroprene, 2,3-dimethyl butadiene-1,3-piperylene, divinyl ketone and esters such as diethyl maleate and diethyl fumarate.

Other exemplary thermoplastics are polyethylene, polybutylene, polypropylene, nylon, polycarbonates, polystyrene, polyvinylacetate, polyvinylidene chloride, polyacrylates.

An equally preferred group of polymers includes the rubbery polymers of butadiene and its homologs as well as copolymers and terpolymers of butadiene and its homologs with copolymerizable monomers. Illustrative comonomers include vinyl aromatics, e.g., styrene, acrylic comonomers, e.g., acrylonitrile, methyl methacrylate and similar materials. Exemplary rubbery polymers which are included within the scope of materials which are flame-retarded in accordance with this invention include polysulfide rubber, polybutadiene, polyiosprene, polychloroprene, butyl rubber, nitrile rubber, propylene/ethylene rubber, styrene-butadiene rubber and similar materials.

The resins and cellulosic materials described above are used to make films, sheets, foams, carpet backing components and other articles of manufacture.

Thermosetting polymers or resins which may be flame retarded in accordance with this invention include phenolic resins such as phenol-aldehydes, polyesters such as polyethylene terephthalate, polyadipates, polyazulates, urea formaldehyde resins, polyvinyl butyral, epoxies, polyamides and similar materials.

Natural polymers which are flame retarded in accordance with this invention include cellulose esters, e.g., cellulose acetate and cellulose nitrate, ethyl cellulose, cork and wood flour products, paper, cloth, cotton and similar cellulosic materials and natural rubber.

In the formulation of plastisol compositions of the present invention, the vinyl resin is uniformly dispersed in a mass of fluid plasticizer. The fluidity of plastisols is influenced in part by the particular resin selected, the plasticizer and the ratio of plasticizer to resin. Plastisols become less fluid as the ratio of plasticizer to resin is reduced. The viscosity of plastisol compositions can also be reduced by the addition of small amounts of a diluent such as benzene, toluene, methyl ethyl ketone, petroleum solvents such as naphtha and similar materials. Plastisols which have been diluted by the addition of such materials are known as "organosols" and are herein included in the term "plastisol". Plastisol compositions ordinarily contain from about 40 to about 120 parts plasticizer per 100 parts resin, with about 60 to about 100 parts plasticizer per 100 parts resin being particularly effective for foamable coatings.

The reaction products of this invention are conveniently added to plasticizers to impart flame retardant and smoke suppressant characteristics thereto. Typical plasticizers to which the reaction products of the invention may be added include phthalates, e.g., dioctyl phthalate, dicyclohexyl phthalate, diundecyl phthalate, butyl benzyl phthalate, phthalates prepared from mixtures of $C_7$, $C_9$ and $C_{11}$ alcohols, adipates, polymerics, e.g., oligoesters, petroleum oils, e.g., naphthenic and paraffinic petroleum oils, natural oils, e.g., soya and linseed oils and their epoxidized derivatives, trimellitates, aromatic extender oils and equivalent, conventionally used plasticizers. resorcinol dibenzoate, diphenyl phthalate, phenyl benzoate, o-tolyl benzoate, eugonol, guaiacol, and complexes of metals such as barium, cadmium, strontium, lead and tin. Suitable heat stabilizers include sulfides and sulfites of aluminum, silver, calcium, cadmium, magnesium, lead carbonate, lead sulfate, lead phthalate, barium oxide, barium-cadmium complexes and similar materials. Normally the compositions contain about 0.5 to about 5 parts stabilizer per 100 parts resin.

When foamable compositions are desired, the plastisol utilized may contain an effective amount of blowing agent. The larger the amount of blowing agent, within practical limits, the greater is the expansion of the foam. About one-half to 10 parts of blowing agent per 100 parts resin is particularly effective for the production of foams of a density which is most desirable as carpet and upholstery materials, although larger amounts may be used. Foam densities of from about 12 to about 40 pounds per cubic foot can be readily obtained. Of course, foams may be prepared by using compressed gas or by mechanically beating or frothing. Each method for producing a foam is particularly useful for specific aspects of industrial usage.

When a chemically blown foam is desired, the blowing agents which are used to provide the foam may be any of those blowing agents well known and readily available to those skilled in the art. Thus, typical blowing agents include oxides, bicarbonates, substituted nitroso compounds, substituted hydrazides, acid azides and similar materials having a nitrogen to nitrogen linkage which decomposes at elevated temperatures to yield an inert gas high in nitrogen.

It is common practice to add accelerators to the plastisol compositions to accelerate decomposition when chemical blowing agents are utilized. Typical accelerators include various metal salts such as dibasic lead phosphite, zinc laurate, zinc oxide, zinc stearate and cadmium octoate. These agents may also serve a dual function as stabilizers for the plastisol compositions.

Fillers are frequently employed to lower the cost of the finished material and to modify its properties. Tupical fillers include calcium carbonate and magnesium silicate. When fillers are employed in the compositions they are generally present in an amount of up to about 150 parts by weight of filler per 100 parts by weight of resin formulation.

Where a colored or tinted composition is desired, colorants or color-fast pigments are incorporated. The colorants or pigments will usually be present in an amount of about 1 to about 5 parts by weight to 100 parts by weight of resin.

Surfactants, such as silicones, are normally added to form formulations that are to be mechanically frothed. The surfactants reduce the surface tension of the foam and thereby increase the air or gas entrapment characteristic of the foam.

Additionally, glass-forming inorganic materials such as zinc borate, zinc oxide, lead oxide, lead silicate and silicon dioxide may be added to increase the flame retardant and smoke-generating characteristics of the foam.

While the invention has been described hereinabove with regard to certain illustrative specific embodiments, it is not so limited since many modifications and variations are possible in the light of the above teachings. It is understood therefore that the invention may be practiced otherwise than as specifically described without departing from the spirit and scope of the invention.

What is claimed is:

1. Reaction product of a phosphite/phosphonate of the formula

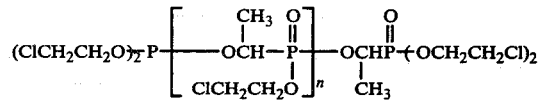

, wherein n has a value from 0 to 4, and a metal compound selected from the group consisting of a metal oxide and a metal salt.

2. Product of claim 1 wherein n has a value of 1.

3. Product of claim 1 wherein n has an average value of 2.

4. Product of claim 1 wherein said metal compound is a metal oxide.

5. Product of claim 1 wherein said metal compound is a metal salt.

6. Product of claim 1 wherein said metal is cobalt.

7. Reaction product of a mixture of (A) a phosphonate of the formula

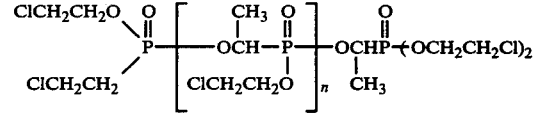

, wherein n has a value from 0 to 4, and (B) a phosphite/phosphonate of the formula

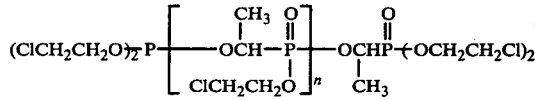

, wherein n has a value from 0 to 4, with (C) a metal compound selected from the group consisting of a metal oxide and a metal salt.

8. Product of claim 7 wherein n has a value of 1.

9. Product of claim 7 wherein n has an average value of 2.

10. Product of claim 7 wherein said mixture is comprised of about 99 percent of said phosphonate.

11. Product of claim 7 wherein said metal compound is a metal oxide.

12. Product of claim 7 wherein said metal compound is a metal salt.

13. Product of claim 7 wherein said metal is cobalt.

* * * * *

UNITED STATES PATENT AND TRADEMARK OFFICE
CERTIFICATE OF CORRECTION

PATENT NO. : 4,133,823

DATED : January 9, 1979

INVENTOR(S) : Samuel F. Joyce, III, Albert W. Morgan, Norman W. Touchette, and William Vanderlinde It is certified that error appears in the above-identified patent and that said Letters Patent are hereby corrected as shown below:

On the cover page of this patent, under Related U.S. Application Data, 3rd line, the number "223,275" should read -- 223,295 --.

In column 4, line 27, the word "lad" should read -- lead --.

In column 5, line 25, the word "Phosphouus" should read -- Phosphorus --.

In column 5, line 34, the number "2,058,941" should read -- 3,058,941 --.

In column 6, line 42, the number "1" (second occurrence) should read -- 2 --.

In column 11, first table, 4th column, line 27, the chemical term "SrCl4" should read -- $SrCl_2$ --.

Signed and Sealed this

Third Day of April 1979

[SEAL]

Attest:

RUTH C. MASON
Attesting Officer

DONALD W. BANNER
Commissioner of Patents and Trademarks